(12) United States Patent
Kelly et al.

(10) Patent No.: US 6,469,223 B2
(45) Date of Patent: *Oct. 22, 2002

(54) SELECTIVE HYDROGENATION OF DIENES

(75) Inventors: Kevin Peter Kelly, Friendswood; James Roy Butler, Houston, both of TX (US)

(73) Assignee: Fina Technology, Inc., Houston, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/477,516

(22) Filed: Jan. 4, 2000

(65) Prior Publication Data

US 2002/0002315 A1 Jan. 3, 2002

(51) Int. Cl.$^7$ .............................. C07C 7/163; C07C 5/02
(52) U.S. Cl. ..................... 585/259; 585/260; 585/261; 585/262
(58) Field of Search .................. 585/259, 260, 585/261, 262

(56) References Cited

U.S. PATENT DOCUMENTS

| | | | |
|---|---|---|---|
| 3,234,298 A | | 2/1966 | van Zijll Langhout et al. |
| 3,238,269 A | | 3/1966 | Holmes et al. |
| 3,301,913 A | | 1/1967 | Holmes et al. |
| 3,662,015 A | | 5/1972 | Komatsu et al. |
| 3,670,041 A | * | 6/1972 | Juhl et al. ............... 260/674 H |
| 3,696,160 A | * | 10/1972 | Chomyn ................. 260/677 H |
| 3,726,936 A | * | 4/1973 | Pitzer .................... 260/677 H |
| 3,804,916 A | | 4/1974 | Lalancette |
| 3,900,526 A | | 8/1975 | Johnson et al. |
| 3,919,341 A | | 11/1975 | Germanas et al. |
| 4,024,077 A | | 5/1977 | Engelhard et al. |
| 4,078,011 A | | 3/1978 | Glockner et al. |
| 4,177,217 A | | 12/1979 | Janoski et al. |
| 4,227,993 A | | 10/1980 | Engelhard et al. |
| 4,417,089 A | | 11/1983 | Drake |
| 4,716,256 A | | 12/1987 | Johnson et al. |
| 4,734,540 A | | 3/1988 | Gattuso et al. |
| 4,906,602 A | * | 3/1990 | Schneider et al. .......... 502/304 |
| 5,030,779 A | * | 7/1991 | Hoxmeier et al. .......... 585/262 |
| 5,043,498 A | | 8/1991 | Ishii et al. |
| 5,087,780 A | | 2/1992 | Arganbright |
| 5,208,405 A | * | 5/1993 | Cheung et al. ............ 585/274 |
| 5,561,197 A | | 10/1996 | Rempel et al. |
| 5,705,571 A | | 1/1998 | Tsiang et al. |
| 5,925,717 A | | 7/1999 | De Boer et al. |
| 6,124,514 A | * | 9/2000 | Emmrich et al. ........... 585/261 |

* cited by examiner

Primary Examiner—Bekir L. Yildirim
(74) Attorney, Agent, or Firm—Gilbreth & Associates

(57) ABSTRACT

A process is provided for the selective hydrogenation of dienes from a mixed hydrocarbon stream. The catalyst contains nickel in an amount between approximately 5 and 15 weight percent and, alternatively, may contain nickel oxide and molybdenum oxide in an amount between approximately 3 to 6 and 12 to 25 weight percent, respectively. The catalyst metals are on an aluminum oxide support. The process does not require any activation or pretreatment of the catalyst. No sulfur is added to the reaction zone and the catalyst is not adversely affected by the presence of up to 0.20% by weight of sulfur in the feed stream. According to the process, conjugated dienes are reduced by at least 80 to 90%.

10 Claims, 3 Drawing Sheets

SELECTIVE HYDROGENATION OF DIENES

TECHNICAL FIELD OF THE INVENTION

This invention relates to a process for the selective hydrogenation of dienes from a mixed hydrocarbon stream.

BACKGROUND OF THE INVENTION

Recent legislation, including the Clean Air Act, has made gasoline reformulation a priority. The driving force continues in research to try to find ways to produce cleaner burning fuels to minimize harm to the environment. Motor fuel components that comprise high concentrations of undesirable elements are under scrutiny as members of the public and private sectors strive to reduce or eliminate such elements.

One of those fuel components under scrutiny is the naphtha stream coming from the fluid catalytic cracker unit ("FCCU") in the refinery. FCCU naphtha is the source of many elements alleged to be harmful to the environment and generally contains significant amounts (greater than 1%) of conjugated dienes and alkynes, as well as sulfur. It is desirable to reduce or eliminate these components in FCCU naphtha before it is introduced to the next stage of refinery processing, for example, to an etherification or alkylation unit.

FCCU naphtha may be used as the feed stream to an etherification unit in order to make tertiary amyl methyl ether (TAME). TAME, used in reformulated gasoline, boosts the octane rating of gasoline. When FCCU naphtha is used as a feed stream for the production of TAME, the dienes and alkynes present in the feed share a tendency to polymerize on the reaction catalyst, causing catalyst deactivation. This results in having to shut down the unit and regenerate or replace the catalyst, which is costly both in terms of production time and catalyst. Therefore, it is important to minimize the amount of dienes and alkynes in the feedstream to the etherification unit.

Another important use for the FCCU naphtha stream is to feed an alkylation unit in a refinery. Alkylation produces alkylate, one of the best gasoline blending components because of its high octane and low vapor pressure. As with etherification, feed impurities adversely affect the alkylation catalyst, causing deactivation. In an alkylation process, the reaction catalyst is an acid. The amount of impurities, such as dienes, in the feed dictate the makeup requirements for the acid, such that a certain amount, n, of impurities in the feed will require an amount of additional makeup acid, i.e. some multiple of n, for the reaction to effectively proceed. FCCU naphtha often contains approximately about 1% or more of dienes. Even this small amount of dienes in the feed stream to the alkylation process has been widely recognized as being undesirable. For a general description of an alkylation process, reference is made to Meyers, *Handbook of Petroleum Refining Processes*, 2d Edition, 1997, pages 1.3–1.7.

Butadiene is a common impurity in alkylation plant feeds. Butadiene tends to polymerize and form acid soluble oils, which increase acid makeup requirements. As butadiene levels resulting from catalytic cracking operations tend to be high, it is important to selectively hydrogenate the dienes and the diolefins without hydrogenating the valuable monoolefins.

As described above, the diolefinic elements in the feed streams to the etherification and alkylation units cost time and money. It is therefore desirable to convert the diolefinic components in the cracked gasoline to monoolefinic components prior to introducing the feed to an etherification or alkylation unit.

It is well known that diene-containing cracked gasoline and other light cracked hydrocarbon oils can be selectively hydrogenated by passing these materials over a suitable hydrogenation catalyst in the presence of hydrogen. It is also well known that suitable hydrogenation catalysts contain nickel, molybdenum, palladium, and other metals, including precious metals, supported on a carrier. The prior art, however, indicates that when using a one of the aforementioned hydrogenation catalysts that the catalysts are preferably sulfided or otherwise pretreated with sulfur to moderate activity and increase selectivity.

For example, U.S. Pat. No. 3,234,298 to Langhout et al. teaches the use of sulfided nickel on alumina catalyst for a selective hydrogenation of diene-containing cracked hydrocarbons. U.S. Pat. No. 3,472,763 to Cosyns et al. teaches that a nickel oxide catalyst on alumina may be used for selective hydrogenation, and that it is preferable to pretreat the catalyst with a sulfur compound and specifies pore size distributions. U.S. Pat. No. 3,919,341 to Germanas et al. is pertinent for its teaching of a sulfided nickel on alumina composite. U.S. Pat. No. 3,301,913 to Holmes and Pitkethly teach the use of a nickel catalyst wherein a portion of the nickel is combined with sulfur. U.S. Pat. No. 4,227,993 to Englehard et al. discloses the use of catalyst comprising platinum, tin and other metals wherein it is advantageous to presulfide the catalyst to minimize the cracking reactions which tend to occur at the start of the treatment.

Other references in the prior art teach the introduction of a component in addition to the feed stream to facilitate selective hydrogenation and to prevent catalyst deactivation. For example, U.S. Pat. No. 3,662,015 to Komatsu et al. teaches a nickel on alumina selective hydrogenation catalyst in which the process includes passing an amount of carbon monoxide along with the feed stream and hydrogen to the hydrogenation reaction zone. U.S. Pat. No. 3,900,526 to Johnson et al. teaches the use of metallic arsenide and antimonide hydrogenation catalysts, with the option of introducing carbon monoxide as a modifier. U.S. Pat. No. 3,238,269 to Holmes teaches the addition of a sulfur-containing compound to the feed stream mixture.

All of the aforementioned U.S. patents and literature references are incorporated herein by reference.

As can be seen from the above, the art is replete with hydrogenation processes. As can also be seen from above, the addition of sulfur to either the catalyst or to the feed stream to promote the hydrogenation process is common. However, the addition of sulfur to the catalyst or to the feed stream to maintain catalyst activity can create an unnecessary sulfur removal problem when the selectively hydrogenated products are to be further processed in other catalytic reactors in which minute amounts of sulfur are detrimental. Thus, it would be desirable to provide a selective hydrogenation process that does not require additional sulfur, either as a component in addition to the feed stream or to the catalyst.

In addition to limiting the amount of sulfur involved in the hydrogenation process, the necessary elements for commercial success of any such process include keeping the process as simple as possible, reducing the costs of the necessary materials, i.e. the catalyst, and making the process as efficient as possible in hydrogenating mixed hydrocarbon feed streams.

Accordingly, it would be desirable to provide a selective hydrogenation process in which, to save time and money, the catalyst does not require an activation or pre-treatment step.

It would also be desirable to provide a selective hydrogenation process in which a readily available and economically efficient catalyst were used in order to avoid the use of precious metal catalysts, which are expensive and susceptible to deactivation due to sulfur contamination.

Further, it would be desirable to provide a selective hydrogenation process in which the catalyst is resistant to typical catalyst poisons such as sulfur and which can be used for sustained periods without significant regeneration.

It would also be desirable to provide a selective hydrogenation process wherein conjugated dienes in FCCU naphtha are at least 80 to 90% removed.

Accordingly, the inventors have discovered the use of a commercially available catalyst that is suitable for selective hydrogenation of dienes such that conjugated dienes are removed to below a readily detectable limit, wherein the catalyst is not expensive, and does not require any activation or pretreatment step, wherein sulfur normally present in the feed stream presents no adverse effect, and no component in addition to the feed stream (and a hydrogen environment in a reaction zone) are necessary for hydrogenation. With these and other important discoveries, the present invention provides a significant improvement over the prior art.

SUMMARY OF THE INVENTION

In accordance with the present invention, there is provided a novel process for the selective hydrogenation of conjugated dienes in a mixed hydrocarbon stream comprising essentially hydrocarbons as would be found in a fluid catalytic cracking unit (FCCU) naphtha stream, wherein activation or pre-treatment of the catalyst is not required and the removal of sulfur, a potential catalyst poison, from the feed stream is not required.

According to one aspect of the invention, a reaction zone is established having a hydrogenation catalyst. The catalyst may comprise nickel on an aluminum oxide support or nickel oxide and molybdenum oxide on an alumina support. A mixed hydrocarbon feed stream is introduced to the reaction zone and passed over the catalyst. Hydrogen is introduced as a co-feed to the reaction zone. The reaction zone is operated at temperature and pressure conditions to effect the selective hydrogenation of conjugated dienes. Finally, an effluent stream, in which at least 80 to 90% of the conjugated dienes have been removed, is recovered from the reaction zone.

BRIEF DESCRIPTION OF THE FIGURES

Further aspects of the invention and their advantages will be discerned when one refers to the following detailed description as taken in conjunction with the figures, in which.

DETAILED DESCRIPTION OF THE INVENTION

Figure 1:
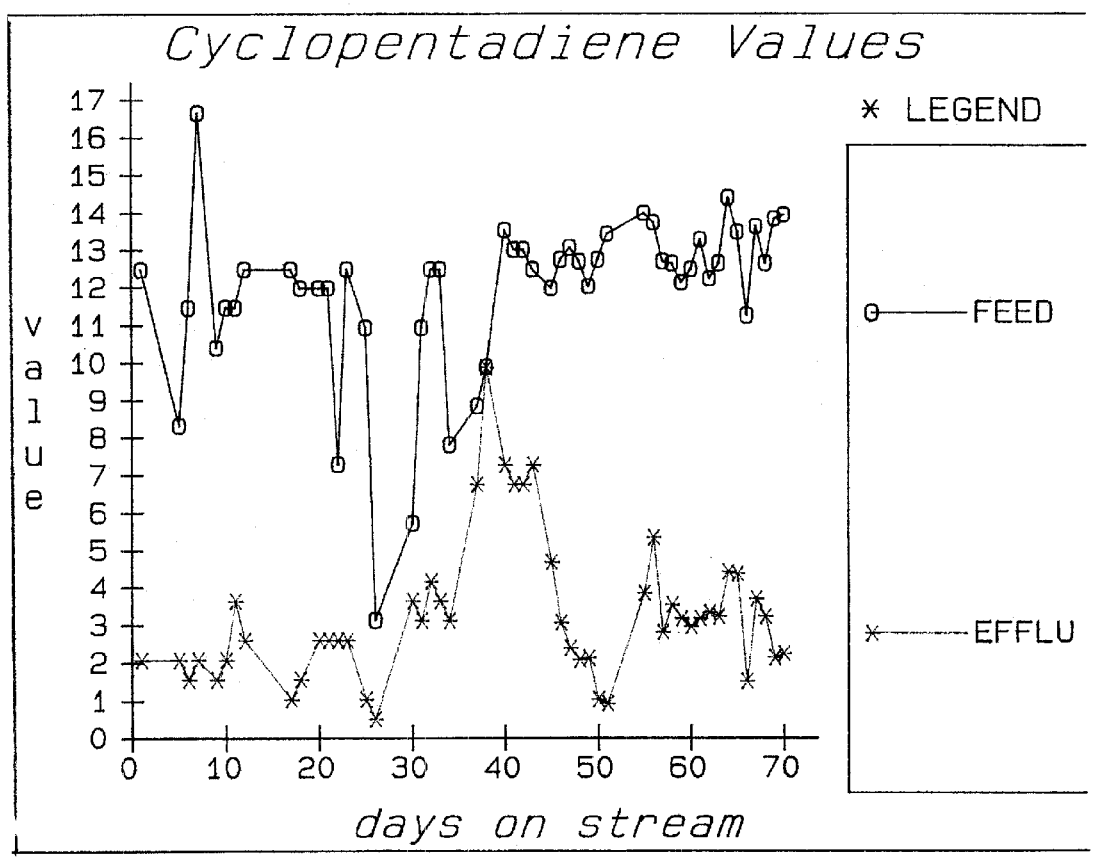
FIG. 1 is a graph illustrating the concentration of conjugated dienes, reported as cyclopentadiene equivalents, for both the feed and effluent versus time/days on stream for the nickel on aluminum oxide catalyst.

The process of hydrogenation of conjugated dienes, according to the present invention, involves a novel application of a hydrogenation catalyst comprising nickel on aluminum oxide or nickel oxide and molybdenum oxide on alumina. No catalyst activation or pre-treatment step is necessary. The feed stream for the reaction may be taken directly from the fluid catalytic cracking unit (FCCU) in a refinery. The process according to the present invention is not adversely affected by any sulfur normally present in the FCCU naphtha stream. Alternatively, the feed stream may be any mixed hydrocarbon stream comprising 5 to 15 carbon atoms.

According to the present invention, a nickel on aluminum oxide catalyst, used commerically for the selective hydrogenation of pyrolysis gasoline, and a nickel oxide and molybdenum oxide on alumina catalyst, a common hydrogenation catalyst, were tested for selective hydrogenation of conjugated dienes in the FCCU naphtha stream.

Sufficient hydrogen must be fed to the reactor to maintain the catalyst in the active form because hydrogen is lost from the catalyst by the hydrogenation process. Generally, the amount of hydrogen relative to FCCU naphtha feed to the reaction zone is between 100 and 1000 standard cubic feet per barrel (SCF/B) and preferably about 300 SCF/B.

According to the process of the present invention, it has now become possible to selectively hydrogenate conjugated dienes in the presence of up to 0.20% by weight of sulfur using a nickel hydrogenation catalyst. In contrast to the prior art, the process of this invention does not require pre-treatment or pre-activation of the catalyst, nor does the process require the removal of sulfur, a potential catalyst poison, from the feed stream. Also in contrast to the prior art, the process of this invention eliminates the need to use precious metal catalysts in the hydrogenation of conjugated dienes, which catalysts are expensive and markedly susceptible to deactivation due to sulfur contamination.

The present invention is particularly useful in carrying out the selective hydrogenation of conjugated dienes, including 1,3-butadienes, without the need for pre-treating or pre-activating the catalyst or removing sulfur from the feed stream to the hydrogenation reaction zone. At least 80 to 90% of the conjugated dienes are removed in the process according to the present invention.

The present invention resulted from two studies. The first used a nickel on aluminum oxide catalyst and was conducted over a period of 70 days. The second used a nickel oxide and molybdenum oxide on alumina catalyst and was conducted over a period of 23 days. In each of the studies, the catalysts were loaded into a reaction zone. In the presence of hydrogen gas, a naphtha stream taken directly from the FCCU was introduced to the reaction zone. Amounts of up to 0.20% by weight of sulfur in the naphtha stream did not adversely affect the catalysts' performance. In each case, conjugated dienes were reduced by at least 80 to 90%.

The experimental work described as follows is provided to illustrate the invention in accordance with the principles of the invention, but is not to be construed as limiting the invention.

EXAMPLE 1

In the experimental work that follows, a mixed hydrocarbon stream comprising essentially hydrocarbons as would be found in an FCCU naphtha stream was used as the feed stream.

The hydrogenation catalyst used in this example was Criterion 204, a commercial nickel on aluminum oxide (Ni/Al$_2$O$_3$) catalyst, obtained from Criterion Catalyst, Houston, Tex.; however, any catalyst containing similar characteristics could be used. The catalyst contained about 10% by weight of nickel.

A vertical reactor of 20 mm inner diameter was packed with 36 ml of the Ni/Al$_2$O$_3$ catalyst. The mixed hydrocarbon feed stream in liquid phase was continuously introduced into the reactor, along with hydrogen at the rate of approximately 160 ml/minute (300 SCF/B). The experiment was run in an upflow mode. The reactor conditions, which were similar to those characteristic of a naphtha hydrotreater except for temperature, are shown below in Table 1.

TABLE 1

| Temperature | 400 and 500° F. |
|---|---|
| Pressure | 450 psi |
| LHSV | 5.25 hr.$^{-1}$ |
| Catalyst Volume | 40 ml (61-2) |
| Liquid Flow | 3.5 ml/min |
| Gas Flow | 120 ml/min (225 SCF/B) |

Feed and effluent were analyzed for conjugated dienes by the maleic anhydride reaction, where maleic anhydride was added to the samples and reacted to form a Deils-Alder product, UOP method 326-82, a method that is well known in the art. Under this method, excess maelic anhydride was hydrolyzed to maleic acid and titrated with sodium hydroxide. A blank was run using the same amount of maleic anhydride as charged to the reaction flash. The amount reported as having reacted with the sample, the diene value, was the net value obtained after correction for the blank. The diene value was used to calculate the number of cyclopentadiene (CP) equivalents.

As noted above, the diene removal reaction, initiated by heating the reactor under liquid flow, was run in an upflow mode. No catalyst activation or pre-treatment was used. At the start of the run, the reduction in the amount of conjugated dienes, from feed to effluent, ranged between 80 and 90%. For the first three weeks, feed concentrations of diene averaged between 10 and 13 mg of CP equivalents per gram of sample. Effluent concentrations averaged between 1.5 and 2.5 mg of CP equivalents per gram of sample. These results are illustrated in FIG. 1.

During the run, the nickel on aluminum oxide catalyst was subjected to several upsets due to pump failures or loss of hydrogen. The catalyst proved unexpectedly resilient. For example, at day 10, the reactor partially lost hydrogen supply. The consequent rise in the effluent concentration of conjugated dienes can be seen in FIG. 1. However, once the hydrogen supply was restored, the concentration of conjugated dienes in the effluent decreased. Subsequently, on days 35 and 39, the feed stream pump failed. As a result, the catalyst had the opportunity to absorb the FCCU naphtha at 400° F. for long periods of time. As would be expected, the olefins and dienes began polymerizing on the catalyst. However, once liquid flow was restored, the effluent was tinged a yellow color and the conversion of conjugated dienes was drastically reduced. At about day 45, the catalyst was regenerated and the catalyst performance was comparable to start of the run performance.

Catalyst regeneration was performed with the reactor in the downflow mode. Although the hydrogen flow to the reactor zone remained unchanged during regeneration, the feed pump was switched off. After regeneration, flow was switched to upflow and the feed pump was restarted to initiate the diene removal reaction.

Feed pump function was lost again on day 51 and on day 55 a regeneration cycle was performed. Again, after regeneration, catalyst performance was comparable start of the run performance. Accordingly, although the catalyst was fouled due to polymerization on the catalyst and sulfur contamination during unscheduled shut downs, the effects were readily reversible with in-situ regeneration, illustrating the robust nature of the catalyst.

Feed and effluent were analyzed periodically for total sulfur. Throughout the testing, feed and effluent sulfur levels were approximately equivalent, indicating a steady state of concentration of sulfur existed on the surface of the catalyst.

Figure 2:
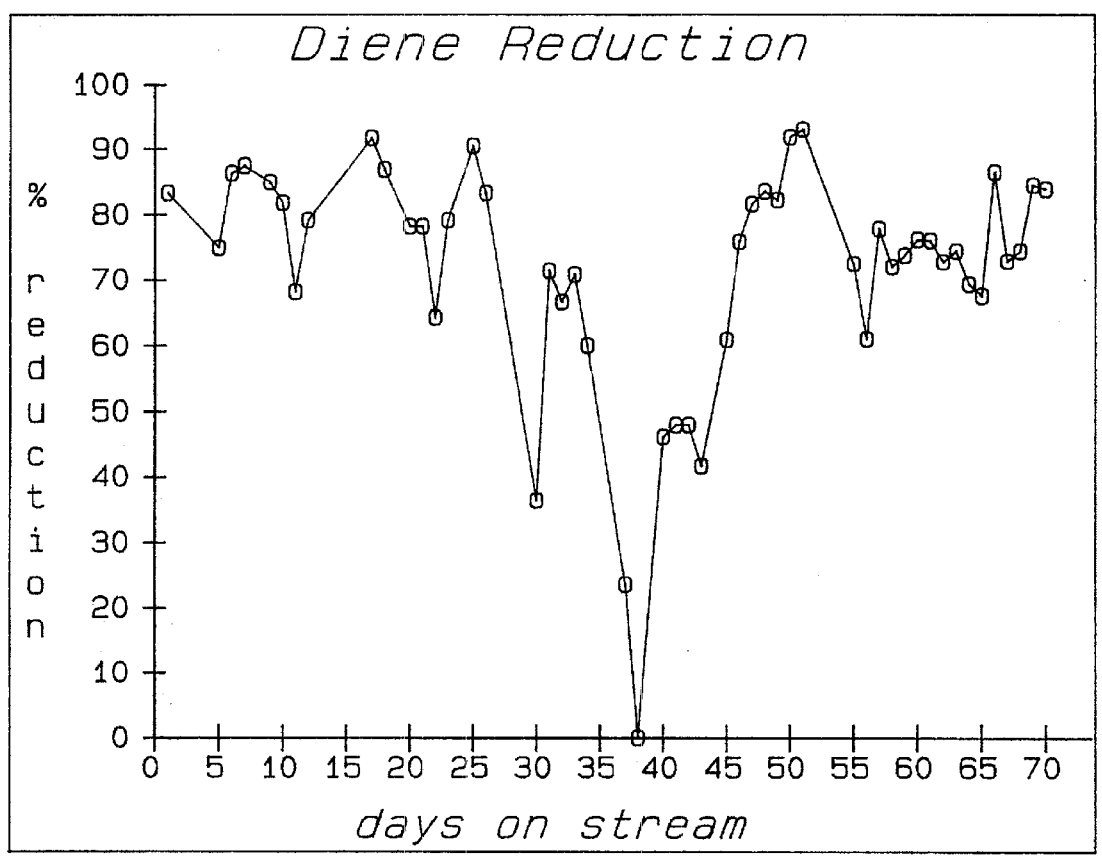
FIG. 2 is a graph illustrating diene reduction measured in percent, comparing diene values in the effluent to those in the original feed, versus time/days on stream for the nickel on aluminum oxide catalyst.

Turning now to FIG. 2, it can be seen that diene conversion was between 80 and 90% for the start and end of the run. The data show that the prolonged presence of 0.15 to 0.20% by weight of sulfur in the feed stream did not adversely affect catalyst performance.

PIONA component analyses were performed on the feed and effluent to determine the olefin content, octane number, and extent of cracking, if any. Feed content of olefins ranged from 34 to 35% by weight. Effluent content of olefins averaged about 2% less. Although the loss of olefins was significant, it was not excessive considering that olefins concentration was 50 to 70 times greater than the concentration of conjugated dienes.

Accordingly, the catalyst unexpectedly effected selective hydrogenation of conjugated dienes in FCCU naphtha, with reduction of conjugated dienes by 80 to 90%. The catalyst was not deactivated by the presence of sulfur in the feed stream. Loss of catalyst activity due to polymerization and other fouling was reversible, regeneration was performed in-sito and catalyst activity was restored with a hot hydrogen sweep.

EXAMPLE 2

The selective hydrogenation was carried out using the same feed as in Example 1, but with a hydrogenation catalyst comprising nickel oxide and molybdenum oxide on alumina (Ni/Mo—Al$_2$O$_3$). An appropriate catalyst could be obtained from a variety of sources, including Akzo in Houston, Tex. In this example, the catalyst used was Katalco 161-2 from Katalco in Houston, Tex. The catalyst contained approximately 4.5% and 18.5% by weight nickel oxide and molybdenum oxide, respectively.

Again, a first vertical reactor of approximately 20 mm inner diameter was packed with approximately 40 ml of the Ni/Mo—Al$_2$O$_3$ catalyst. It was run in an upflow mode consistent with Example 1. The reactor conditions are shown in Table 2.

TABLE 2

| Temperature | 400° F. |
|---|---|
| Pressure | 450 psi |
| LHSV | 5 hr.$^{-1}$ |
| Catalyst Volume | 36 ml |
| Liquid Flow | 3 ml/min |
| Gas Flow | 160 ml/mm (300 SCF/B) |

The outlet from the first reactor was connected to a second reactor, which contained zinc oxide. Zinc oxide is available from many commercial sources, including Akzo, Criterion and UCI, Inc. The second reactor was run in a downflow mode to give a continuous gas phase for H$_2$S removal. The second reactor was used for the purpose of attempting to remove sulfur from the stream. Although the example was unsuccessful at sulfur removal, diene removal was favorable.

As in Example 1, feed and effluent were analyzed for conjugated dienes by the maleic anhydride reaction. Dienes were removed to a level at or below the readily accepted detection level. PIONA component analyses, also as performed in Example 1, were repeated for this Example 2. Results of the PIONA component analyses showed a decrease of approximately one octane number.

Figure 3:
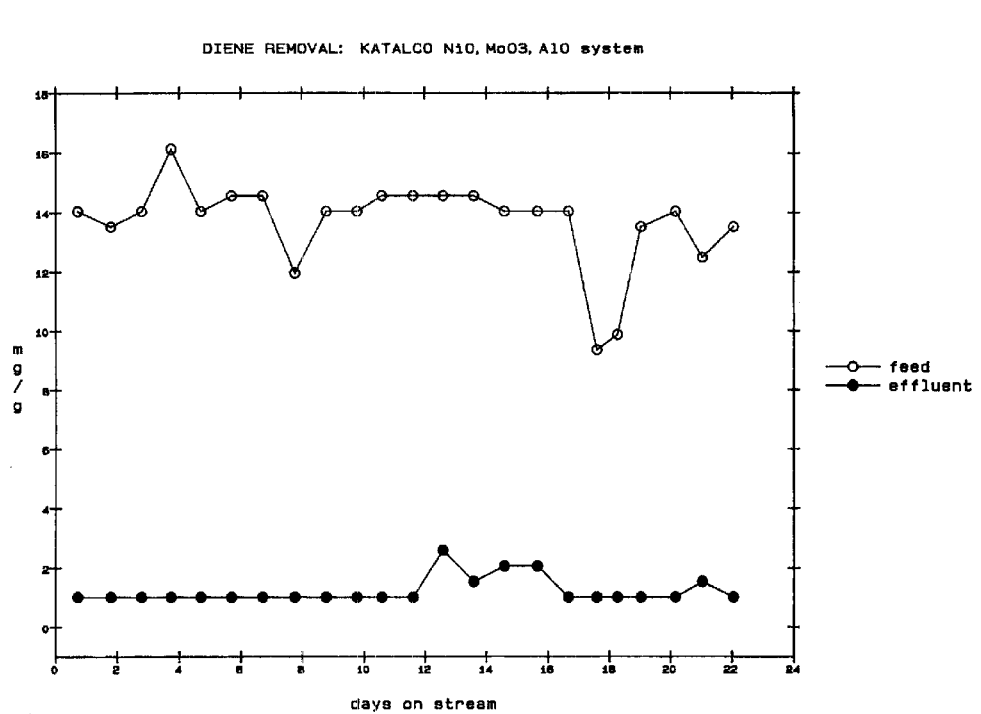
FIG. 3 is a graph illustrating the concentration of conjugated dienes, reported as cyclopentadiene equivalents, for both the feed and effluent versus time/days on stream for the nickel oxide and molybdenum oxide on alumina catalyst.

Turning again to the figures, FIG. 3 graphically illustrates the concentration of conjugated dienes, reported as cyclopentadiene (CP) equivalents, for both the feed and effluent versus time/days on stream. As shown, the average concentration of 14 mg of CP equivalents per gram of sample in the feed was reduced to below the detection limit of 1–2 mg of CP per gram of sample. No catalyst deactivation was observed during the run.

Analysis of both the feed and effluent for total sulfur showed that after the first day on stream, these concentrations were nearly equal, even after the temperature was raised to 500° F. at the end of the run. (The temperature was raised in an unsuccessful attempt to activate sulfur removal activity.) It would be expected that if any sulfur had been converted to $H_2S$, it would have been removed in the second reactor with the ZnO bed. This was in agreement with the hydrogen balance around the reactor. After accounting for the total removal of conjugated dienes, the remainder of the hydrogen was unreacted.

Accordingly, both the nickel on aluminum oxide and nickel oxide and molybdenum oxide on alumina catalysts unexpectedly effected selective hydrogenation of conjugated dienes in FCCU naphtha, with reduction of conjugated dienes by at least 80 to 90%. Neither catalyst required an activation or pre-treatment step, nor did the reaction require additional sulfur either as a component of the feed stream or incorporated into or on the catalyst. The catalysts were not adversely affected by up to 0.20% by weight of sulfur in the feed stream and the presence of sulfur in the feed stream did not have a detrimental effect on the removal of dienes. Additionally, the catalyst was easily regenerated as necessary.

While the invention has been described with reference to particular embodiments thereof, it will be apparent to those skilled in the art that various changes and modifications can be made without departing from the spirit of the invention or from the scope of the appended claims.

What is claimed is:

1. A process of selectively hydrogenating dienes present in a mixed hydrocarbon feed stream comprising essentially hydrocarbons in the range of 5 to 15 carbon atoms or a naptha stream from a fluid catalytic cracking unit in a refinery, said process comprising the steps of contacting said fee in a reaction zone in the presence of hydrogen at selective hydrogenation conditions with a non-pretreated catalyst consisting essentially of nickle oxide and molybdenum oxide on an alumina support and recovering an effluent stream from said reaction zone, wherein said effluent stream contains at least 80 to 90% less conjugated dienes than said mixed hydrocarbon feed steam.

2. A process according to claim 1, wherein said catalyst contains an amount of nickel oxide within the range of 3 to 6% by weight and an amount of molybdenum oxide within the range of 12 to 25% by weight.

3. A process according to claim 2, wherein said catalyst contains amounts of nickel oxide and of molybdenum oxide which are approximately 4.8 and 18.5% by weight, respectively.

4. A process according to claim 1, wherein said mixed hydrocarbon feed stream is passed over said hydrogenation catalyst at a rate sufficient to provide a liquid hourly space velocity of approximately 2 to 15 hour$^{-1}$.

5. A process according to claim 1, wherein said reaction zone is operated at a temperature within the range of 150 to 300° C. and at a pressure within the range of 300 to 600 psig.

6. A process of selectively hydrogenating dienes present in a mixed hydrocarbon feed stream comprising essentially hydrocarbons in the range of 5 to 15 carbon atoms or a naptha stream from a fluid catalytic cracking unit in a refinery, said process comprising the steps of contacting said feed in a reaction zone in the presence of hydrogen at selective hydrogenation conditions with a non-pretreated catalyst consisting essentially of nickle oxide and molybdenum oxide on an alumina support, wherein said catalyst comprises 3 to 6% by weight nickel oxide and 12 to 25% by weight molybdenum oxide, and recovering an effluent steam from said reaction zone, wherein said effluent stream contains at least 80 to 90% less conjugated dienes than said mixed hydrocarbon feed stream.

7. A process according to claim 6, wherein said catalyst contains amounts of nickel oxide and of molybdenum oxide which are approximately 4.8 and 18.5% by weight, respectively.

8. A process according to claim 6, wherein said mixed hydrocarbon feed stream is passed over said hydrogenation catalyst at a rate sufficient to provide a liquid hourly space velocity of approximately 2 to 15 hour$^{-1}$.

9. A process according to claim 6, wherein said reaction zone is operated at a temperature within the range of 150 to 300° C. and at a pressure within the range of 300 to 600 psig.

10. The process of claim 6 wherein said mixed hydrocarbon feed steam comprises up to about 0.20% by weight sulfur.

* * * * *

UNITED STATES PATENT AND TRADEMARK OFFICE
CERTIFICATE OF CORRECTION

PATENT NO.     : 6,469,223 B2
DATED          : October 22, 2002
INVENTOR(S)    : Kevin P. Kelly and James R. Butler It is certified that error appears in the above-identified patent and that said Letters Patent is hereby corrected as shown below:

Column 7,
Line 55, "fee" should be -- feed --; and

Column 8,
Line 7, "steam" should be -- stream --.

Signed and Sealed this

Eighteenth Day of March, 2003

JAMES E. ROGAN
*Director of the United States Patent and Trademark Office*